(12) United States Patent
Zamecnik et al.

(10) Patent No.: US 10,533,947 B2
(45) Date of Patent: Jan. 14, 2020

(54) ENCAPSULATED DYE COATED NOBLE METAL NANOPARTICLES WITH INCREASED SURFACE ENHANCED RAMAN SCATTERING PROPERTIES AS CONTRAST AGENTS (71) Applicants: Colin R Zamecnik, Albany, CA (US); Gilbert C Walker, Mississauga (CA)

(72) Inventors: Colin R Zamecnik, Albany, CA (US); Gilbert C Walker, Mississauga (CA)

(*) Notice: Subject to any disclaimer, the term of this patent is extended or adjusted under 35 U.S.C. 154(b) by 597 days.

(21) Appl. No.: 14/651,444

(22) PCT Filed: Dec. 11, 2013

(86) PCT No.: PCT/CA2013/050951
§ 371 (c)(1),
(2) Date: Jun. 11, 2015

(87) PCT Pub. No.: WO2014/089698
PCT Pub. Date: Jun. 19, 2014

(65) Prior Publication Data
US 2015/0316481 A1 Nov. 5, 2015

Related U.S. Application Data (60) Provisional application No. 61/735,779, filed on Dec. 11, 2012.

(51) Int. Cl.
G01N 33/543 (2006.01)
G01N 21/65 (2006.01)
C09K 11/06 (2006.01)

(52) U.S. Cl.
CPC ............ G01N 21/658 (2013.01); C09K 11/06 (2013.01); G01N 33/54393 (2013.01)

(58) Field of Classification Search
None
See application file for complete search history.

(56) References Cited

U.S. PATENT DOCUMENTS 7,985,539 B2 * 7/2011 Mirkin ................ C12Q 1/6816
435/6.1
2011/0144307 A1 6/2011 Miao et al.

FOREIGN PATENT DOCUMENTS

WO 2005062741 7/2005
WO 2012094727 7/2012

OTHER PUBLICATIONS

Huang et al., Preparation of silica-encapsulated hollow gold nanosphere tags using layer-by-layer method for multiplex surface-enhanced raman scattering detection. Langmuir 2011, vol. 27, pp. 10228-10233. (Year: 2011).*

(Continued)

Primary Examiner — Shafiqul Haq
(74) Attorney, Agent, or Firm — Hill & Schumacher (57) ABSTRACT The present disclosure provides semiconductor-metal composite nanoparticles with optical properties that are superior to those of pure materials for use as contrast agents. The composites include noble metal nanoparticles having a layer of linker molecules being bound to the surface of the noble metal nanoparticle and a layer of dye molecules bound to the layer of linker molecules. The dye molecules are selected such that they form an ordered structure that exhibits a collective absorption band shift, compared to the individual dye molecule, when bound to the noble metal nanoparticle. This structure is encapsulated in a stabilizing coating layer forming a multi-shell structure with properties suitable for biosensing and other detection applications which exhibit enhanced Raman scattering compared to nanoparticles having dye molecules bound thereto not in the ordered structure.

33 Claims, 8 Drawing Sheets (56) References Cited

OTHER PUBLICATIONS

Lim et al. Adsorption of cyanine dyes on gold nanoparticles and formation of J-aggregates in nanoparticle assembly. J. Phys. Chem. B. 2006, vol. 110, pp. 6673-6682. (Year: 2006).*

Akihito Yoshida et al. "Effect of the Interaction between Molecular Exciton andLocalized Surface Plasmon on the Spectroscopic Properties of Silver Nanoparticles Coated with Cyanine Dye J-aggregates", Journal of Physical chemistry c, vol. 114 No. 7, Feb. 25, 2010, pp. 2867-2872.

IP Shell Y et al., "Lipid-encapsulation of surgace enhanced Raman scattering (SERS) nanoparticles and targeting to chronic lymphocytic leukemia (CLL) cells", Frontiers in Biological Detection: from Nanosensors to Systems IV, SPIE, 1000 20th St. Bellingham WA 98225-6705 USA. vol. 8212 No. 1 Jan. 30, 2012 pp. 1-12.

International Search Report in PCT/CA2013/050951 dated Mar. 27, 2014.

Written Opinion in PCT/CA2013/050951 dated Mar. 27, 2014.

* cited by examiner

ENCAPSULATED DYE COATED NOBLE METAL NANOPARTICLES WITH INCREASED SURFACE ENHANCED RAMAN SCATTERING PROPERTIES AS CONTRAST AGENTS

CROSS-REFERENCE TO RELATED PATENT APPLICATIONS

This application is a National Phase application claiming the benefit of the international PCT Patent Application No. PCT/CA2013/050951, filed on Dec. 11, 2013, in English, which claims priority to the U.S. Provisional Patent Application Ser. No. 61/735,779, filed on Dec. 11, 2012, in English, the entire contents of which are incorporated herein by reference.

FIELD

The present invention relates to a method for dye coated noble metal nanoparticles with increased surface enhanced Raman scattering (SERS) properties as contrast agents and the use of these as contrast agents when encapsulated with a lipid bilayer and having target binding agents bound to the outer surface of the lipid layer.

BACKGROUND

Contrast agents are used to assist in the identification of molecular and supramolecular targets or regions with distinctive local state properties. Non-limiting examples of targeted species are proteins, polysaccharides, polynucleic acids and other analytes, or environmental properties. Non-limiting examples of state properties include distinct pH, temperature, and solvent quality. The targeted molecule or state may be difficult to observe in the background of other material, and the contrast agent makes it easier to identify it. One example is a particular type of cell surface protein in the presence of other types of cell surface proteins. Often such proteins are the markers of a health condition, and their identification can assist in diagnosis, determination of treatment or monitoring the progress of a health condition. Contrast agents can be used to detect other species, such as chemical threats or biological and chemical warfare agents.

Optical contrast agents, which function using light, are attractive because the technology to employ them can be relatively simple, for example a light microscope or spectrometer coupled to a sampling device. Brighter optical contrast agents can be easier to detect than less bright agents. Methods to create brighter particles are therefore valuable. It is useful to have contrast agents that can be easily multiplexed, meaning that multiple kinds of contrast agents can be used on the same sample to detect simultaneously the presence and number of multiple targets. For example, the type and number of more than one type of protein might be detected on the surface of a single cell, which could improve in identifying the state of the cell and its relevance to the health of the individual. Optical contrast agents that can be multiplexed, which means optical contrast agents that can be used in the presence of other different contrast agents, are therefore valuable.

Plasmonic nanomaterials, and their utility in surface enhanced chemical and biological sensors, have garnered immense interest in the past two decades due to their size-dependent optical properties and potential as target specific contrast agents. Surface-enhanced Raman spectroscopy (SERS) is the most widely studied and offers the possibility of single molecule detection.

Raman scattering nanoparticles are potentially useful as optical contrast agents because they exhibit sharper optical signatures than, for example, most fluorescent contrast agents. This means that they can in principle be highly multiplexed. Raman scattering by isolated molecules is, however, weak, and therefore methods to create brighter or more strongly scattering Raman contrast agents would be useful.

Raman-scattering nanoparticles have great promise as sensitive detection labels. However, due to complex design criteria such as binding specificity, robust colloidal stability in biological environments, and optical sensitivity, few commercially viable sensor systems have been generated as a result of this widespread research.

Active plasmonics, defined as plasmonic structures coupled to materials that can interact with the plasmon, has generated significant interest, especially in the past few years, as a next generation platform to address the need for brighter SERS signals. J-aggregates, Rhodamine 6G, cytochrome c, porphyrin derivatives, and host-guest charge transfer complexes have all been successfully coupled to plasmonic nanostructures to elicit a much brighter surface-enhanced resonance Raman (SERRS) signal. Even greater enhancement has been achieved when a wavelength matching approach is employed to couple the molecular and plasmonic resonances together with the excitation field. Appropriate coordination of multiple resonating entities offers a powerful tool for brighter SERS-based sensing platforms. However, while these other approaches have demonstrated some improvement to the optical brightness, incorporation into a robust and stable detection label modality has not been accomplished.

For practical use of nanoparticles as a detection modality, stability in various solutions and shelf life are of paramount importance. While in water, these particles may exhibit desirable properties, but when placed in biological media or buffer solution, they tend to aggregate very quickly and optical properties are greatly diminished as a result. Often, smaller particles are employed during complicated surface chemistry, as they are more resistant to aggregation due to electrostatics, i.e. when charged species or proteins are introduced into solution and around the particle. However, smaller particles have much weaker plasmon resonances, so there is an effective trade-off between particle stability and effective optical brightness to make the composite particles useful as contrast agents.

Several ways to increase the long term stability of larger SERS-active nanoparticles have been proposed, the most popular being the co-adsorption of various PEG chain lengths to the surface of the particle along with the Raman dye. Recently, encapsulation of the Raman dye within a stabilizing to coating layer that surrounds particles has been employed for relatively large particles of 60 nm in diameter. These stabilizing layers can consist of inorganic oxides such as silicon or titanium, or organic self-assembled structures such as lipid vesicles. These composite particles have shown great promise as shelf-stable, biologically compatible biosensors, as the stabilizing coating prevents particle aggregation in biological media while offering a versatile platform for targeting functionality and other surface chemistry.

SUMMARY

The present disclosure provides an exitonic semiconductor noble metal composite nanoparticle for enhanced Raman scattering, comprising:

a noble metal nanoparticle having a surface;

a layer of linker agents being bound to the surface of the noble metal nanoparticle;

a layer of dye molecules having an absorption band and being bound to the layer of linker agents, said dye molecules being selected such that they form an ordered structure that exhibits a collective absorption band shift when bound to the noble metal nanoparticle; and a stabilizing coating layer encapsulating the noble metal nanoparticle with the linker layer and the ordered structure of dye molecules to produce an encapsulated composite nanoparticle;

wherein said encapsulated composite nanoparticle exhibits enhanced Raman scattering compared to nanoparticles having dye molecules bound thereto not in said ordered structure.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION

Generally speaking, the embodiments described herein are directed to lipid encapsulated dye coated noble metal composite nanoparticles, in which the dye forms an ordered structure, which exhibit increased SERS signals. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific method, structural and functional details disclosed herein are not to be interpreted as limiting but merely as a basis for the claims and as a representative basis for teaching one skilled in the art to variously employ the present invention.

Definitions

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

As used herein, the terms "comprises", "comprising", "includes" and to "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

As used herein, the word "linker" or phrase "linker molecule" refers to a species that joins a molecular or molecular aggregate shell to the metal nanoparticle.

As used herein, the word "bound" means joined by covalent or non-covalent bonding, and therefore includes, but is not limited to, bonds where electrons are shared or electrostatic and vander Waals interactions, where electrons may not be shared.

As used herein, the phrase "self-assembly" or "supramolecular self-organization" refers to a type of process in which a disordered system of pre-existing components forms an organized structure or pattern as a consequence of specific, local interactions among the components themselves, without external direction. When the constitutive components are molecules, the process is termed supramolecular self-organization or molecular self-assembly.

As used herein, the phrase "J-aggregates" refers to any type of dye with an absorption band that shifts to a longer wavelength (i.e. bathochromic shift) of increasing sharpness (i.e. higher absorption coefficient) when the individual dye molecules aggregate to form an ordered structure. Aggregation may be induced from the influence of solvent, additive or concentration as a result of supramolecular self-organization or self-assembly.

As used herein, the phrase "H-aggregates" refers to any type of dye with an absorption band that shifts to a shorter wavelength (i.e. a hypsochromic shift) upon aggregation. As noted above, aggregation is induced from influence of solvent, additive or concentration as a result of supramolecular self-organization.

The present invention is based on the discovery that multi-shell nanostructures comprised of noble metal nanoparticles and dyes that, when bound to the surface of the metal nanoparticle (or bound to a linker layer bound directly to the surface of the metal nanoparticle) form an ordered structure that exhibits a collective absorption band shift relative to the absorption band of the individual dye molecules. These multilayer structures exhibit novel nonlinear optical properties that can be exploited as a uniquely stable and optically bright sensing platform. It is possible to employ a wavelength matching approach to improve SERS response of the metal nanoparticle when used in conjunction with this ordered dye structure.

Particularly, the inventors have shown that the electric field can be strongly confined within the dye ordered structure (monolayer) when irradiated at the appropriate wavelength as a result of the ENZ phenomenon. We experimentally validated the SERS signal as a result of field intensity by varying the effective distance between the resonating entities. The effect of distance with respect to the particle is demonstrated experimentally at both resonant and non-resonant wavelengths.

EXAMPLE

The basis of the present invention will be presented herebelow showing the modeling of the enhanced effect using an exemplary dye, namely a dye which forms J-aggregates. J-aggregates are one of the most well-studied resonant excitonic species available. Under sufficiently high concentration, or otherwise suitable conditions such as an appropriately charged surface, particular cyanine dye molecules will self-assemble into J-aggregates. J-aggregates generate a collective absorption response that is red shifted from the respective monomeric band, which generates a collective exciton within the aggregate. When these dyes are adsorbed onto noble metal nanoparticles in the J-aggregate assembly, the collective exciton can couple to the surface plasmon, and interfere both destructively and constructively depending on their relative energy level positions. Ultrafast transient state absorption state spectroscopies as well as theoretical quantum mechanical treatment have verified the presence of both weak- and strong-type coupling states between the exciton and plasmon. The resonances of these molecules with various plasmonic nanostructures have been demonstrated previously, and have shown that predictable spectral overlap and energetic coupling is possible. The orientation and adsorption kinetics have also recently been studied in detail, with both thiol-metal bonded and electrostatic-type adsorption.

The epsilon-near-zero (ENZ) effect has recently garnered interest in the field of metamaterials, as a way to tailor various sub-wavelength optical properties. This effect has been predicted to give very large enhancement factors for SERS generating nanoparticles. In this disclosure the inventors present the first use of ENZ J-aggregate materials used in coordination with metal nanoparticles to prepare a SERS sensory platform.

Here, the inventors utilize a dye that is traditionally not a good Raman reporter, but has other unique and useful optical and electrical properties we exploited to generate a large increase its Raman scattering.

Figure 1A:
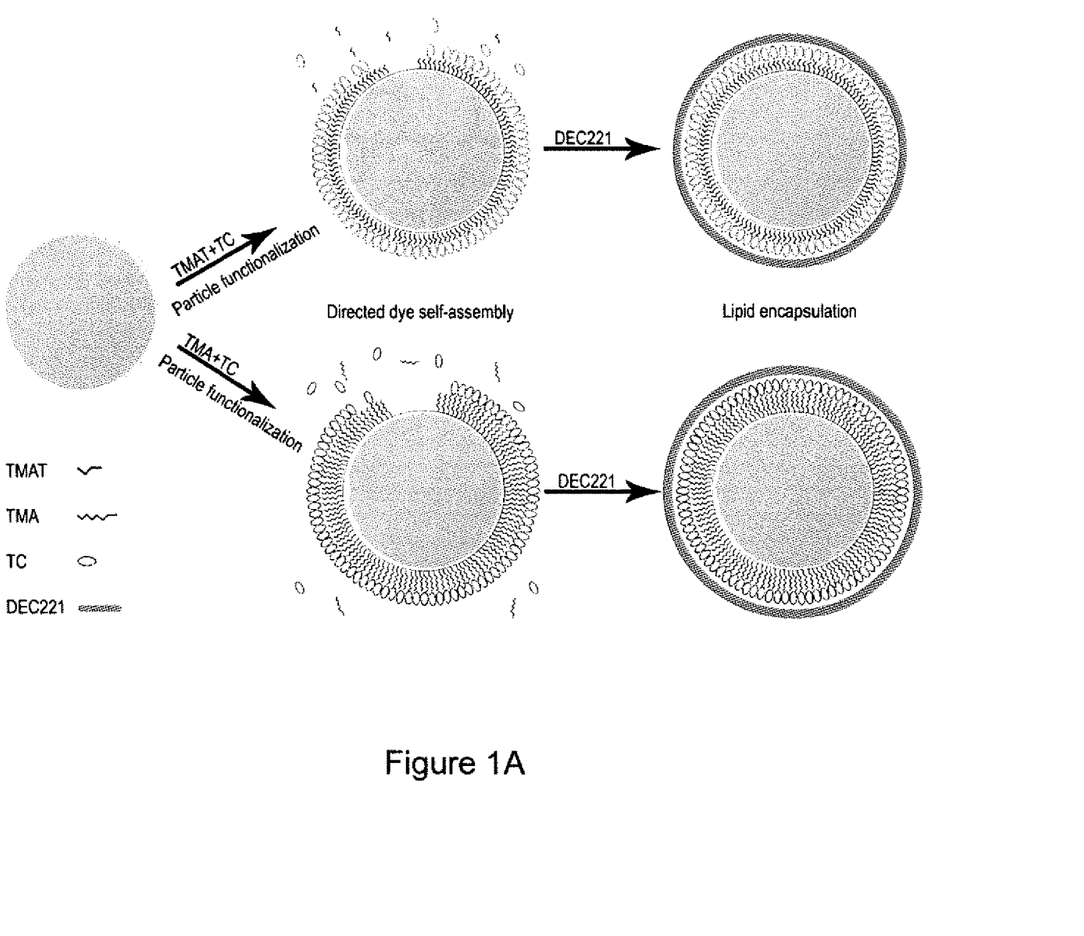
FIG. 1A shows the synthesis of multi-shell J-aggregate plasmonic nanoparticles. Dye and linkers are conjugated in one step, and subsequently lipid encapsulated with DEC221 lipid formulation. Particles are then washed via centrifugation before analysis.
Figure 1B:
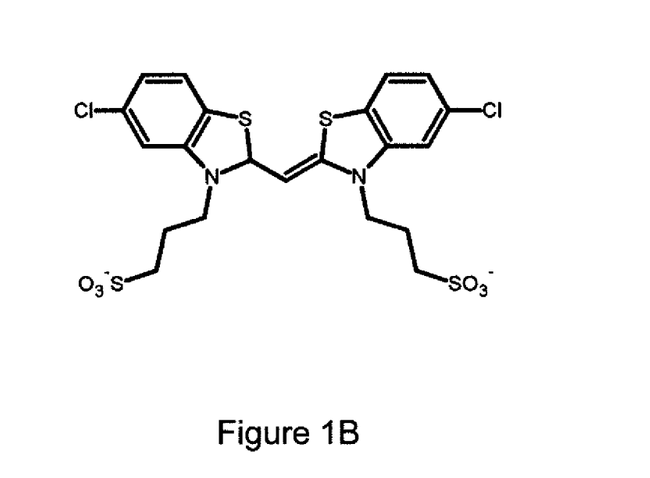
FIG. 1B shows the molecular structure of J-Aggregate forming dye, 3,3'-disulfopropyl-5,5'-dichloro-9-ethyl-thiacarbocyanine sodium salt (TC) used to illustrate the enhanced SERS signal according to the present invention.

The dye used in the preferred embodiment of the invention is 3,3'-disulfopropyl-5,5'-dichloro-9-ethyl-thiacarbocyanine sodium salt (TC). FIG. 1B shows the molecular structure of J-Aggregate forming dye, 3,3'-disulfopropyl-5,5'-dichloro-9-ethyl-thiacarbocyanine sodium salt (TC). However, under suitable conditions, most commonly high concentration, presence of a multivalent cationic salt, or a cationic surface, will precipitate self-assembly of the dye into a J-aggregate. What is special about a J-aggregate is it has its own absorption band which is generated by the excitation of a collectively-shared exciton between π-stacked rings in aggregate. This absorption is very sharp and narrow.

It has been shown previously that if the dye can be made to self-assemble into a J-aggregate on a plasmonic nanoparticle, the exciton from the J-aggregate can couple to the plasmon of the noble metal nanoparticle, given they are sufficiently close enough to one another, in what is known as a Fano resonance.

Experimental Methods

Materials

Acetylthiocholine, silver nitrate, sodium citrate (99.0%) and hydrogen tetracholoroaurate were purchased from Sigma-Aldrich Co. (Canada). Uranyl acetate dehydrate was purchased from Ted Pella, Inc. (USA). N,N,N-trimethyl-(11-mercaptoundecyl) ammonium chloride (TMA) was purchased from ProChimia Surfaces sp z o.o. (Poland). TC, 3,3'-disulfopropyl-5,5'-dichloro-9-ethyl-thiacarbocyanine sodium salt (TC) was ordered from Hayashibara Biochemical Laboratories, Inc. (Japan). Dioleoylphosphatidylcholine (DOPC), egg sphingomyelin (ESM), and ovine cholesterol (Chol) were received from Avanti Polar Lipids (USA). All chemicals were used as received. Water was purified with a Millipore Milli-Q water system to 18.2 MΩ·cm. All glassware was piranha cleaned.

Synthesis of Silver Nanoparticles (NPs)

The synthesis of the silver nanoparticles (AgNPs) followed the reported procedure by Meisel and Lee (Lee, P. C.; Meisel, D. J. Phys. Chem. 1982, 86, 3391-3395) Briefly, 6 mg of $AgNO_3$ was dissolved in 33.3 mL of $H_2O$ and brought to boil at which point 666 μL of 1% sodium citrate was added. The solution was left to reflux for one hour before removing from heat. The final product was a murky greenish yellow. These were diluted 1:3 in water and stored at 4° C. until use.

Thiocholine (TMAT) Synthesis

TMAT was synthesized by simple acid hydrolysis of commercially available acetylthiocholine in a manner similar to Peng et al. (Peng, L.; Zhang, G.; Zhang, D.; Xiang, J.; Zhao, R.; Wang, Y.; Zhu, D. Org. Lett. 2009, 11, 4014-7) 500 mg of acetylthiocholine was dissolved in 15 mL of absolute ethanol and 4 mL of 37% HCl. While stirring, the solution was refluxed at 100° C. for seven hours, after which it was allowed to cool for 30 min. Excess solvent was removed by rotary evaporation under reduced pressure. Recrystallization of thiocholine was carried out in a $H_2O$/isopropanol/ether (0.5 mL/5 mL/25 mL) solvent system. The solution was subsequently chilled in an ice bath for 20 min, recovered by filtration and washed with 25 mL of ether, then allowed to dry. The resultant white product, herein referred to as TMAT, was dried in a desiccator overnight and stored under argon at −20° C. The product's structure was confirmed by NMR (see supporting data) with purity of approximately 90%. $^1$H NMR (400 MHz, $D_2O$) δ 3.76 (t, J=8 Hz, 2H) 3.23 (m, 11H).

Preparation of Ag/Linker/TC Nanoparticles

While stirring, 62.5 μL of 1 mM TC was added to 800 μL of AgNPs. Separately, 62.5 μL of 1 mM TMAT or TMA, respectively, was added to 325 μL of deionized water and stirred. The linker solution was then added to the stirring Au/TC solution and allowed to stir overnight.

Lipid Preparation

Lipids were prepared as per the protocol reported by Ip et al. (Ip, S.; Maclaughlin, C. M.; Gunari, N.; Walker, G. C. Langmuir 2011, 27, 7024-7033) Briefly, in a 3:1 chloroform/methanol solution, DOPC, ESM and Chol were mixed in a 2:2:1 molar ratio (DEC221), respectively, to a final mass of 10.7 mg. One milligram aliquots were placed in glass vials and dried under a stream of argon gas until the solvent evaporated, and a film of lipid was visible on the bottom of each vial. The vials were left to dry under vacuum overnight to remove any remaining solvent, then backfilled with argon and capped. DEC221 lipids were stored at −20° C. until use.

The encapsulation of nanoparticles by lipids was achieved by sonicating nanoparticles in a suspension of multilamellar vesicles (MLV) of DEC221 for 45-60 min at 50° C.

Lipid Encapsulation of J-Aggregate/Nanoparticle Complex

Prior to encapsulation, DEC221 was thawed and hydrated with water to a concentration of 1 mg/mL. The lipids were then warmed in a 50° C. water bath. The lipids were agitated with vortex mixing every 10 min for 30 min until a multilamellar vesicle suspension was formed. The functionalized nanoparticles were then encapsulated by adding 1 mL of particles to 1 mL of the DEC221, and sonicating at 50° C. for 60 min or until clear. Sonication of the MLV under these conditions in the absence of particles has been shown to produce unilamellar vesicles (ULV)<100 nm in diameter (see Lapinski, M. M.; Castro-Forero, A.; Greiner, A. J.; Ofoli, R. Y.; Blanchard, G. J. Langmuir 2007, 23, 11677-11683. And Maulucci, G.; De Spirito, M.; Arcovito, G.; Boffi, F.; Castellano, A. C.; Briganti, G. Biophys. J. 2005, 88, 3545-3550). This transformation can be observed visually; the MLV suspension appears cloudy, while the ULV suspension appears almost clear, since the size of the vesicles in the ULV suspension has become smaller than the diffraction limit of visible light, and consequently scatters significantly less light than the MLV suspension. Here, it is demonstrated that sonication of the MLV suspension in the presence of metal nanoparticles results in nanoparticles being encapsulated by a lipid bilayer.

All dye-lipid-particle products underwent two cleaning steps before any measurements were made. Each cleaning step involved centrifugation of the particle/vesicle suspension at 4500 RPM for 5 minutes using a desktop microcentrifuge. This settled the particles to the bottom of the microcentrifuge tubes, and the supernatant was removed and retained in a separate container. The particles were then resuspended to the same concentration in 18 MΩ-cm water.

Instrumentation and Measurement

UV-Vis Spectroscopy was performed on a Varian Cary 5000 UV-Vis-NIR spectrophotometer. Particles were placed in a 1-cm-path-length black wall cuvette and spectra were collected at a scan speed of 240 nm/s using 18.2 MΩ·cm water as a blank. Spectra were used to confirm the plasmon shift and J-aggregate dip or peak on silver nanoparticles, respectively.

Transmission Electron Microscopy (TEM) was performed on a Hitachi H-7000 TEM instrument operating at 100 kV. Samples were prepared by placing a droplet of aqueous solution containing the particles on the grid. A small droplet of 2% uranyl acetate solution was added to the larger one on the grid, which was then allowed to air dry.

Raman measurements were carried out on a Renishaw InVia Confocal Raman Spectrometer, equipped with a research grade Leica microscope and 50× long-range objective. Coherent 407 nm and 514 nm lasers were used. Data was collected with WiRe 2.0 and analyzed with GRAMS Suite software.

Theoretical Methods

The optical response of the hybrid nanostructure was investigated using finite difference time domain calculations using FDTD solutions (Lumerical Inc). The dielectric function of the TC dye was obtained via extinction cross section of the TC dye in the J-aggregate state. This was easily accomplished by titrating a divalent cationic salt into a 10 µm TC aqueous solution, which gave rise to almost complete J-aggregate formation once the salt concentration reached 1 mM.

For accurate modeling of the thin spacer and J-aggregate layer, a mesh size of 0.3 nm is used. The simulation domain is terminated by perfectly matched layer (PML) for minimal reflections. To calculate the absorption and scattering cross sections of the hybrid structure, we employed the formalism of the total field scattered field (TFSF).

Results and Discussion

Theoretical Results

In the FDTD calculations, the silver core is modeled by a fit to the experimental data of Palik (Palik, E. D. Handbook of Optical Constants of Solids; Academic press, 1998; Vol. 3) whereas the dielectric constant of the J-aggregate, $\varepsilon_{jagg}$ is modeled using a Lorentz line shape given as follows $$\varepsilon_{jagg} = \varepsilon_\infty + \frac{f\omega_0^2}{\omega_0^2 - \omega^2 - i\omega\gamma_{jagg}} \quad (1)$$

where f is the reduced oscillator strength, $\omega_0$ represents the resonant angular frequency and $\gamma_{jagg}$ is the line width. The permittivity of the modeled J-aggregate layer producing the best fit to the experimental extinction data is shown in FIG. 1a. The following parameters resulted in the best fit to the experimental data: f=0.33, $\omega_0$=4.023×10$^{15}$, $\gamma_{jagg}$=2.4×10$^{14}$ and $\varepsilon_\infty$=1.769. The anisotropy of the J-aggregate response is neglected in this analysis; while this is not rigorous, the behavior is dominated by the radial permittivity component in the quasi-static regime (see supporting information). This is close to the present regime of operation and so we expect little deviation from these calculations for a full anisotropic model.

In this disclosure the inventors exploit the epsilon near zero (ENZ) phenomenon. It is noted that the real part of $\varepsilon_{jagg}$ approaches zero at a wavelength of 435 nm. This effect can result in strong local field enhancement at the interface between two different materials, as dictated by the boundary condition $\varepsilon_1 E_1 = \varepsilon_2 E_2$, where $\varepsilon_i$ and $E_i$ (i=1, 2) are the permittivity and normal component of the electric field at the interface. Thus as the permittivity of one medium approaches zero, the field strength in that medium is expected to increase significantly. However, it should be noted that the maximum enhancement achievable is limited by the non-zero imaginary part of $\varepsilon_{jagg}$.

Figure 1C:
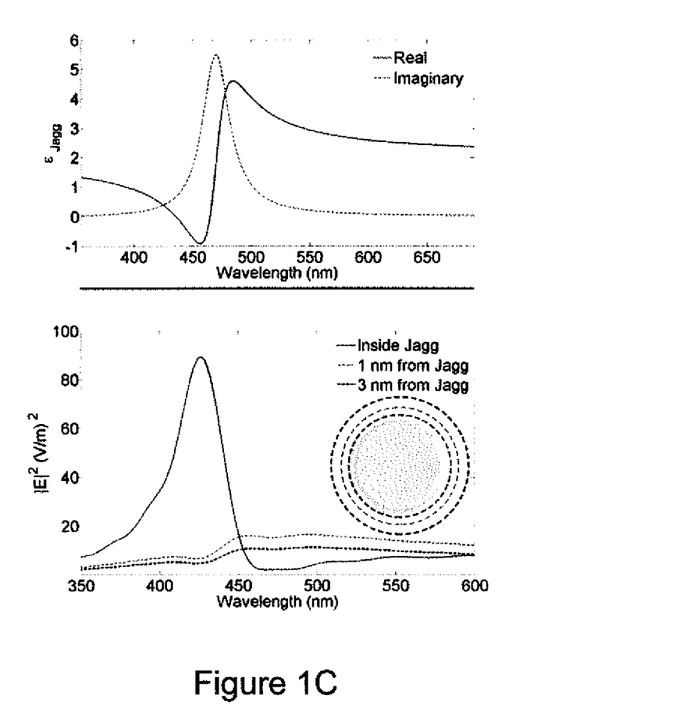
FIG. 1C: Top—Modeled dielectric constant of the J-aggregate layer. Bottom—Field as a function of wavelength for 40 nm diameter particle, 0.5 nm linker and 1 nm J-aggregate using FDTD method. Field is plotted at r=21.5, 23.5 and 25.5 nm, respectively.

Given that the SERS scattering intensity varies according to the electric field around the particle, the wavelength at which to irradiate the particle was chosen carefully to optimize the ratio between the dielectric constants of the metal and dye. The calculations optimized for the maximum field intensity, and the results are shown in FIG. 1C. The maximum field intensity for the J-aggregate around the silver particle is 420 nm, and is sharply resonant around that wavelength.

In practice, the peak is too narrow to accommodate all Stokes-shifted peaks for the TC dye. We are interested mostly in enhancement of the pump electromagnetic radiation with regards to the plasmonic particle. We therefore chose to irradiate the particle at a wavelength of 407 nm, which falls very close to the plasmon resonance for this particle size, which lies around 410 nm. The brighter Stokes-shifted peaks then fall very close to the field intensity peak. This wavelength matching approach is what gives rise to the large enhancement factors in terms of electromagnetic field around the particle.

Figure 4:
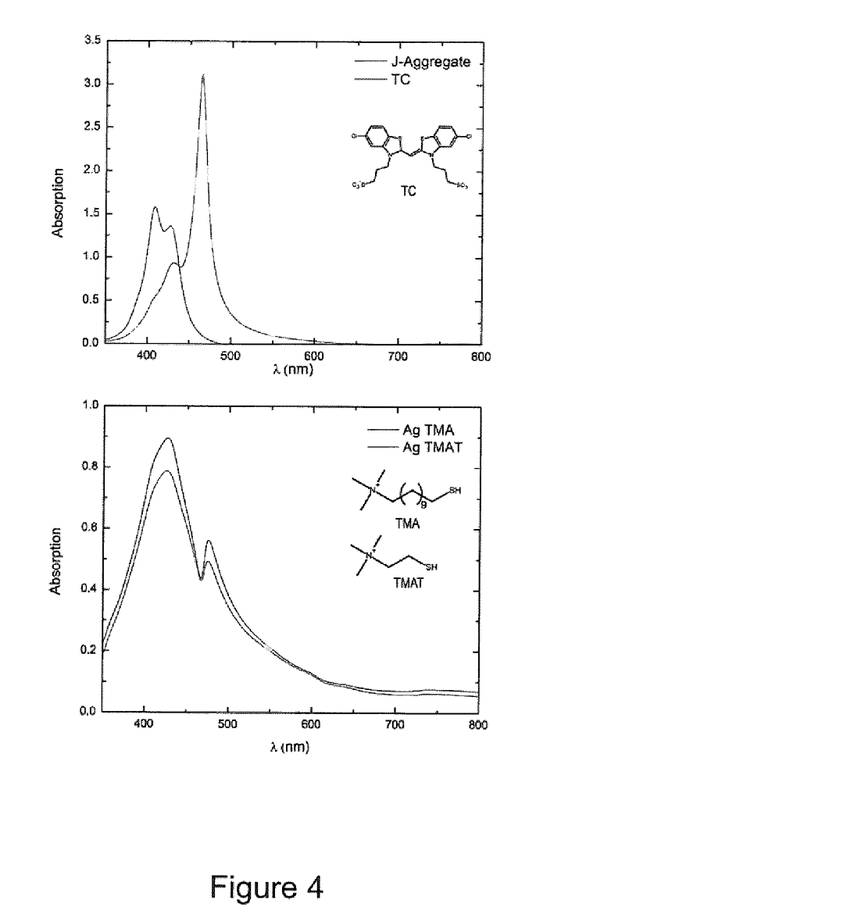
FIG. 4: Top—UV-Vis spectra of J-aggregate and TC. Inset: Molecular structure of dye. Bottom—UV-Vis spectra of J-aggregate AgNPs with TMAT and TMA spacer layers. Inset: Molecular structures of cationic linkers.

To summarize, the following steps are followed to determine the optimum excitation wavelength to irradiate nanoparticles to give the enhanced SERS signals:

The dielectric constant, ε, is calculated from the absorption cross section for the dye in its aggregated state, (here we used UV-Vis), calculation as shown in top of FIG. 1C, absorption data shown in FIG. 4 (top, red curve). This is done by inducing some free, monomeric dye into aggregates (ordered structures) by adding some salt. No particles are in these spectra. It is assume the self-assembled structure is the same as the one that forms on the particle, and therefore use that as the model dielectric for the calculations/simulations).

It is then observed where the real portion of the dielectric constant is close to zero. The imaginary portion of the dielectric constant is responsible for unwanted absorption, and therefore should also be minimized. The wavelength that optimizes these effects is identified as the target wavelength, as shown in top of FIG. 1C to be ~425 nm for the example above.

Generate a particle that has a plasmon resonance near this wavelength, this is done by tuning geometry or composition of the particle The dielectric constant of the metal is then obtained from literature data (see Palik reference above)

The field intensity is calculated for the dye-linker-metal composite via FDTD simulation for all wavelengths making use of the boundary condition $\varepsilon_1 E_1 = \varepsilon_2 E^2$, to generate a plot similar to the bottom one in FIG. 1C.

Optimal wavelength is chosen to be one with largest E-field, this is the target irradiation wavelength, which should fall close to the plasmon resonance of the particle Lastly, choose a practical laser (not all wavelengths are possible, obviously) to excite the composite nanoparticles in solution. Prefer to excite the particle as close as possible to this peak in top of FIG. 1C, while ensuring stokes shifted light from Raman scattering still falls within that peak and is enhanced as well.

Figure 2:
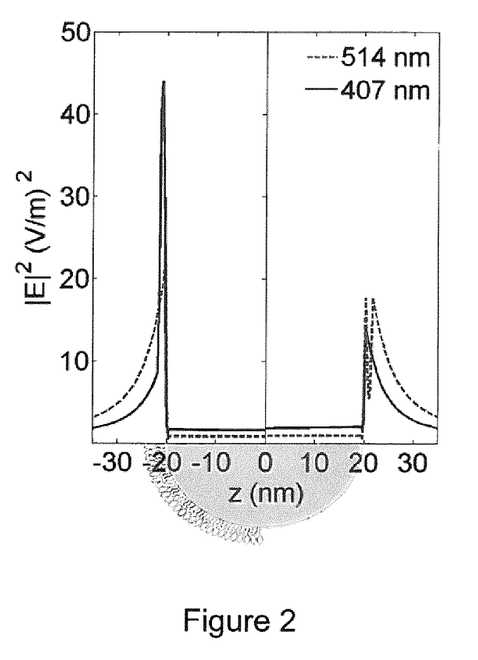
FIG. 2 shows the electric field intensity as a function of distance from the center of the particle. Left side of each plot with 0.5 nm (Thiocholine) TMAT linker and right side is naked (no J-aggregate) for reference.
Figure 3:
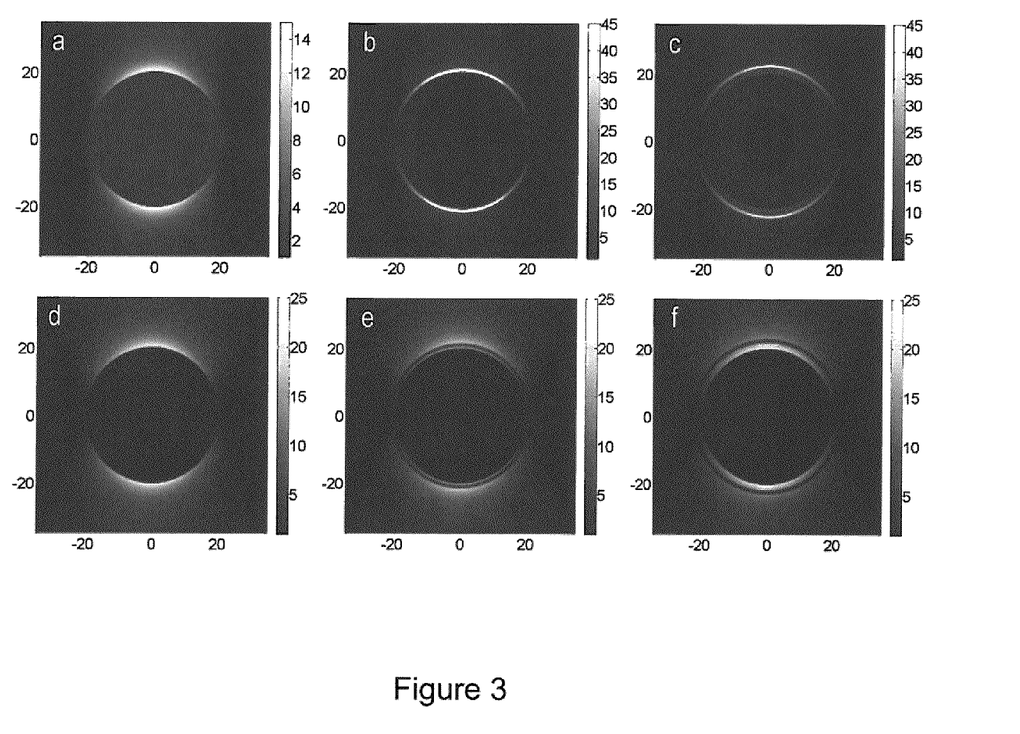
FIG. 3: a) Naked particle, b,c) with TMAT, (trimethyl-(11-mercaptoundecyl) ammonium chloride) TMA linker layers respectively coated in TC J-aggregate. Irradiated at 407 nm. d-f) Irradiated at 514 nm. The electric field is strongly confined within the J-aggregate layer at the 407 nm. The electric field is measured in $(V/m)^2$, and the distance from the centre of the particle in nm.

FIG. 2 shows how the interaction distance between the particle and the J-aggregate dye layer affects the field intensity in the particle and dye layer. As expected, the field drop-off is approximately exponential as the layer is further removed from the particle surface. However, we found that the relationship of field strength with respect to distance from the particle is heavily dependent on the wavelength. FIG. 3 demonstrates that at the resonant wavelength, the field intensity is greatly attenuated with respect to distance from the surface. However, at the non-resonant wavelength, the difference is negligible across the distances considered, as the dielectric constant of the J-aggregate dye becomes relatively large at wavelengths red of ~450 nm.

This generates significant field confinement within the J-aggregate dye when irradiated at 407 nm, giving values of |E| of over 800—almost twice the field generated by the surface of the particle with no dye layer present. FIG. 3 shows, however, that there is negligible field enhancement at the non-resonant wavelength of 514 nm, where the dielectric of the dye is comparable to that of the metal. It is the strong confinement within the dye layer as a result of the ENZ phenomenon that gives rise to the large increase in SERS scattering intensity as shown in the following section.

Experimental Results

The inventors prepared a particle which is able to exploit this unusual optical behavior and generate a strong Raman signature from the J-aggregate dye monolayer that surrounds it. We first synthesized silver nanoparticles which were approximately 40+/−5 nm in diameter, confirmed by TEM. These were then functionalized with the J-aggregate layer. Given the lack of chemistry available to bind this particular dye to the surface of the particle, we employed a cationic linker similar to Kometani et al, (Yoshida, A.; Yonezawa, Y.; Kometani N. Langmuir 2009, 25, 6683-9) which directed the TC dye to self-assemble on the surface of the particle in the J-aggregate state. This strategy is applicable to any anionic J-aggregate forming dye. In order to improve particle stability, the functionalized particles were then encapsulated within a lipid bilayer. An outline of the synthetic route to generate these particles is shown in FIG. 1A. The plasmon peaks and generation of the J-aggregates were confirmed via UV-Vis, as shown in FIG. 4. Two different lengths of linker were used in order to validate the relationship between field enhancement and distance of the J-aggregate from the silver particle surface.

The shortest linker, TMAT, was not commercially available, and was instead synthesized by acid hydrolysis of an acetylthiocholine precursor. The multi-layer particles were functionalized by the dye and spacer layer without particle aggregation. In addition to the characteristic 'peak' of the J-aggregate in the UV-Vis spectra, its presence was confirmed by ζ-potential measurements and visually identified via HRTEM. J-aggregates did not form on as-synthesized citrate-capped particles that were not functionalized with a cationic linker.

The particles functionalized with the TMA linker had a somewhat sharper J-aggregate peak in the UV-Vis spectra compared to the TMAT functionalized particles. Given the more favourable enthalpic interactions between the aliphatic portions of the longer TMA molecules in comparison to the very short TMAT molecule, we postulate that there was greater SAM density when using the longer linker. Given a discrete charge per linker molecule, the TMA functionalized AgNPs were better able to accommodate J-aggregate formation of the anionic TC dye, which in turn generates a larger peak in the UV-Vis spectrum for these particles.

Figure 5:
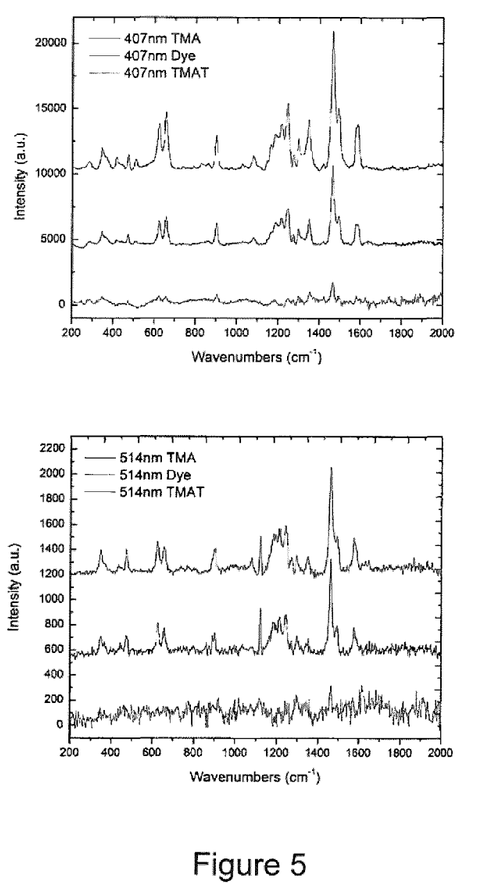
FIG. 5 shows Surface-Enhanced (resonance) Raman Spectra of the J-aggregate functionalized AgNPs. No significant background generated by the lipid bilayer.

The SERS spectra of the two types of particles are shown in FIG. 5. TC has been previously shown to give a rather weak Raman signature at traditional pump wavelengths (Kitahama, Y.; Tanaka, Y.; Itoh, T.; Ishikawa, M.; Ozaki, Y. Bull. Chem. Soc. Jpn. 2009, 82, 1126-1132) with some improvement as the dye excitation grows close to the J-aggregate resonance near the 458 nm wavelength. The strong peaks in the 400-1000 $cm^{-1}$ region are indicative of J-aggregate formation within the proximity of the particle. This is due to enhancement of out of plane vibrational modes of the Albrecht A term through the resonance Raman effect. FIG. 5 demonstrates SERRS signal at the resonant wavelength of 407 nm is over an order of magnitude greater in intensity as compared to the particles irradiated at the off resonant wavelength, and considerably brighter than when irradiated at wavelengths of 458 and 488 nm.

The SERS intensity difference between different separation distances from the surface of the particle also closely followed simulations. The TMAT and TMA molecules were approximated to be 0.5 and 2 nm in length, respectively, and the J-aggregate monolayer thickness is approximately 1 nm. The relationship between Raman scattering intensity, I, and field intensity, |E|, is often approximated to be I∝|E|⁴. The ratio of the field strengths at the two distances as calculated by the FDTD simulations is 1.15. We can calculate the experimental value for the ratio of the field intensity using the following equation, $$(I_{TMAT}/I_{TMA})=(|E|_{TMAT}/|E|_{TMA})^4. \quad (2)$$

Using the average ratio of the peak height between the two thicknesses was taken over eight major peaks across the spectrum, the ratio of the field strengths was found to be approximately 1.14, which agrees well with the values generated by theory. However, at 514 nm, we see a negligible difference in terms of optical brightness between the two spacer layers, once again in accordance with the FDTD simulations performed.

It is interesting that while there may have been a greater amount of dye on the surface of particles functionalized with the TMA in comparison to the TMAT, the signal generated seems to be much more strongly related to the distance between the dye layer and the particle, as seen in the significantly brighter SERS spectrum for the TMAT functionalized particles at 407 nm.

Encapsulation with Stabilizing Coating

Figure 6:
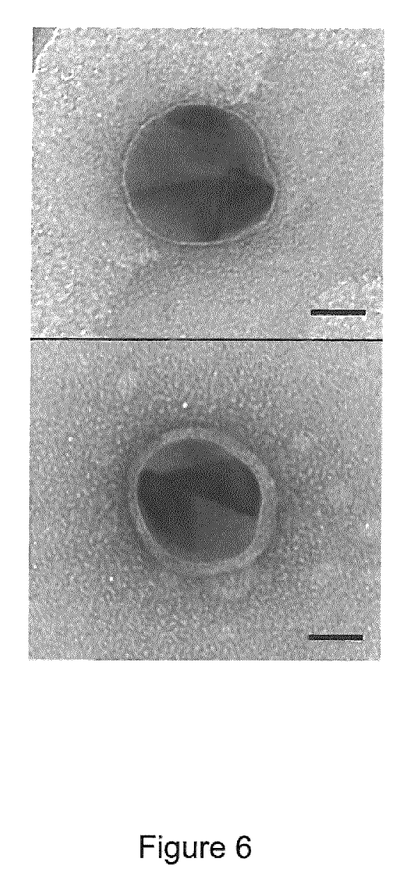
FIG. 6 shows typical negative-stain TEM images. Top—Linker/J-aggregate functionalized AgNPs, bottom—functionalized particles after lipid encapsulation. Lipid bilayer appears larger than expected due to partial fusing with grid upon sample drying. Scale bar is 20 nm.

The encapsulation of these particles was performed with a lipid mixture of sphingolipid and cholesterol, which produced robust particles that proved mechanically stable over the course of several months. TEM images of the particles with and without the lipid bilayer around the particle are shown in FIG. 6. The particles settled somewhat over the course of several weeks, but were easily resuspended with simple shaking of the vial they were contained in.

The vesicle confers several advantages to this platform over 'naked' particles. Firstly, the particles can be washed and excess dye can be removed from solution, something that is impossible to do without the presence of the vesicle to prevent rupture of the J-aggregate monolayer. This allows facile removal of excess dye from solution, reducing toxicity in biological systems. Likewise, the presence of the bilayer also 'traps' the J-aggregate dye within it, preventing interaction with other species which may induce undesired chemical or biological effects, while preventing degradation of optical properties due to breakup of the multi-shell nanoparticle structure.

The lipid vesicle surrounding the particle is an ideal platform for further modification, be it other Raman dyes or targeting moieties. These can easily be accommodated within the vesicle either by covalent attachment to the lipid anchor or physical incorporation into the aliphatic portion of the bilayer.

Figure 7:
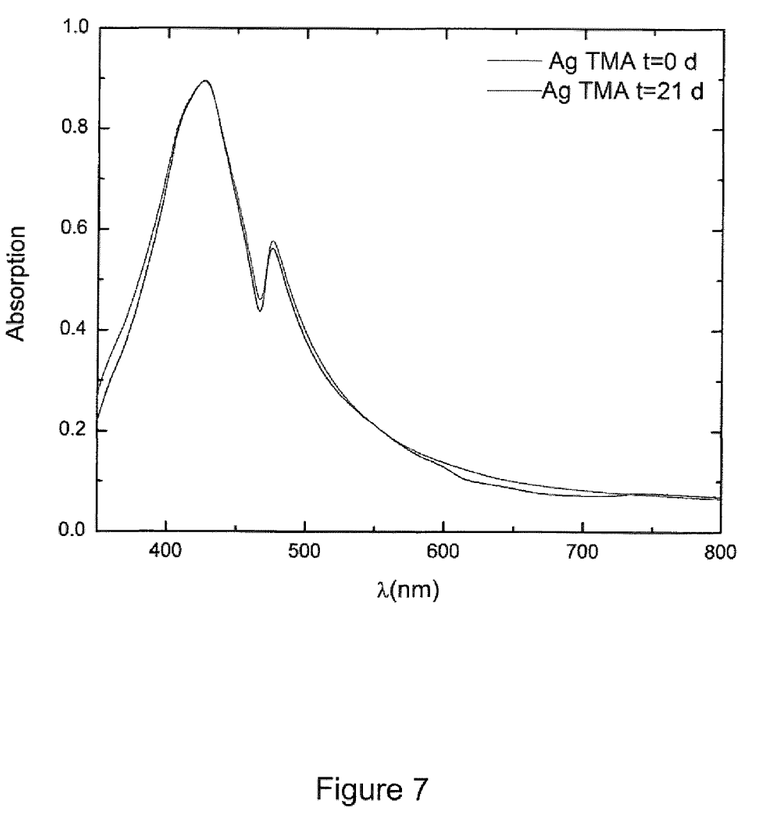
FIG. 7 is a UV-Vis plot of the lipid-encapsulated nanoparticles, comparing the spectra 0 days and 21 days after synthesis. This demonstrates the temporal stability of the particles and how the dye retains the supramolecular structure over a realistic period of time on the shelf.

The lipid encapsulation of these J-aggregate functionalized particles entraps the dye monolayer within the vesicle, and prevents dye leakage from the particle, as shown in FIG. 7. This allows for limited interaction of the dye with other species in solution, and simultaneously promotes mechanical stability of the complex. These model SERS particles serve as a platform to generate solution-stable biosensors for cell surface marker detection and other applications.

The above non-limiting exemplary example used silver nanoparticles, the dye 3,3'-disulfopropyl-5,5'-dichloro-9-ethyl-thiacarbocyanine sodium salt (TC) which forms the J-aggregate structure on the silver nanoparticles, the linkers thiocholine (TMAT) and TMA and a stabilizing coating layer prepared from DOPC, ESM and Chol were mixed in a 2:2:1 molar ratio, it will be appreciated by those skilled in the art that these are only examples and many alternatives of each may be used as discussed below.

Noble Metal Nanoparticles

Nanoparticles of the invention can be composed of materials other than gold nanoparticles. The nanoparticles are noble metal nanoparticles and may be gold, silver, copper, nickel, palladium, platinum, ruthenium, rhodium, osmium, iridium, or an alloy of any of the foregoing metals. In vivo applications require that the SERS moiety to be biocompatible, and in such applications, the preferred metal would likely be silver or gold, but might also be an alloy of gold and silver, or gold and platinum, or core-shell structures of two metals where the shell metal is gold. It is possible that a silver particle with a gold coating would be suitable.

In terms of size, nanoparticles suitable for the invention are somewhere between 2 nm to about 1000 nm, but more likely greater than 5 nm and less than 900 nm. Preferably, nanoparticles are between about 5 nm and about 300 nm, or between about 5 nm and about 100 nm. It thought that the most likely to be preferred diameter is between about 20 nm and about 100 nm. A very preferred range is from 20 nm to about 100 nm. While spherical nanoparticles are preferred, other shapes may be used such as elliptically-, or rod-shaped nanoparticles.

Linkers and Linker Lengths

While the linker in the above example is a separate molecule from the dye molecule, it will be appreciated that under certain circumstances the linker may be part of dye molecule itself rather than a separate entity, for example, if the dye contains chemistry such as a thiol group that would allow it to adsorb directly to the particle, but if present can range from 0.1 nm to 10 nm in length. The type of linker could be anionic, cationic or neutral depending on the chemistry of the aggregate forming dye that is used. Potential suitable linker agents include thiocholine, trimethylammonium conjugated alkanethiols, acrylates, NN-trimethyl (alkyl)ammonium, tetrabutylammonium, tetratmethylammonium brominde, cetyltrimethylammonium bromide, citrates, poly methacrylate, ascorbic acid, DNAs, 2-mercaptopropionic acid, 16-mercaptohexadecanoic acid, dodecyl sulfate, amino acides, homocystine, cysteine, and glutathione.

It should also be noted that the dye used in the present system could be incorporated into the lipid bilayer in several ways, for example, but not limited to, through physical linkage to a lipid-molecule, or through physical incorporation into the hydrophobic fatty region between lipid molecules (in a similar manner as cholesterol). It is also feasible to generate a J-aggregate forming dye that generates a multi-layer structure, such as a bilayer that forms around the particle in a manner similar to a lipid bilayer. The dye in this case would exhibit structural similarity to a lipid molecule, in that it would have well-defined hydrophobic and hydrophilic regions that facilitate self-assembly into a vesicle system.

Dyes

Dyes used in the invention can be composed of any type of polymethine dye, where the polymethine dye may be, but not limited to, a cyanine dye, including but not limited to merocyanines, indocyanines, to anthrocyanines, phycocyanine, isocyanines, pseudoisocyanines and thiacyanines; squaraines; perylene bisimides; thiolated aggregate-forming dyes that adsorb directly on the surface of the nanoparticle (and hence include a linking member as part of the dye structure); any of the above in combination, eg. A squaraine and a cyanine conjugated together. Particularly useful dyes include any class of cyanine dye that forms J-aggregates or H-aggregates, or other aggregates in which the collective absorption of the aggregate is different than that of the monomeric species of that dye.

Stabilization Coating Layer

Stabilization coatings of the invention can be composed of organic self-assembled lipid vesicles. These lipid vesicles can consist of sterols, glycerides, sphingolipids and phospholipids, as well as combinations thereof.

Phospholipids are a class of compounds known to those skilled in the art. One type of phospholipid is glycerol-based and includes a headgroup which can be, for example, phosphtidyl glycerol (PG), phosphotidyl choline (PC), phosphatidic acid (PA), phophatidyl ethanolamine (PE), phosphatidyl serine (PS), phosphatidyl inositol (PI), and derivitized/functionalized forms of these such as rhodamine-PE or PEG-PE. The tail groups can be comprised of hydrogen, or an acyl chain such as palmitoyl, myristyol, oleoyl, stearoyl etc. The tail group can consist of two identical groups or two different groups. For example DOPC has two oleoyl acyl chains and a phosphochoine headgroup joined by a glycerol backbone. DOPG has the same acyl chains but a phosphatidylglycerol headgroup. POPC has one palmitoyl and one oleoyl acyl chains and a phosphatidylcholine head group.

Also used in examples described herein was sphingomyelin, a sphingophospholipid. Sphingolipids include sphingosine and its derivatives, including sphingomyelin.

Phospholipids, which include sphingophosoplipids, are known to occur naturally. Included within this definition are other non-naturally occurring phospholipids that are structurally related to certain of the naturally occurring compounds in that they are amphipathic and can form layers for encapsulation of metal nanoparticles. Within the definition of phospholipids are those containing phosphtidyl glycerol (PG), phosphotidyl choline (PC), phosphatidic acid (PA), phophatidyl ethanolamine (PE), phosphatidyl serine (PS), and phosphatidyl inositol (PI) in their headgroup and joined via a glycerol moiety to one or two fatty acyl chains. Each chain can have from 6 up to 24 carbons, and may be branched or unbranched, although they are typically unbranched. Each chain can include one or more double bonds or one or more triple bonds. Chains having 12 to 24 carbon atoms are more preferred.

In a preferred embodiment, the phospholipid component of a SERS complex of the invention is a bilayer.

Examples of particular phospholipids of the invention include dioleoylphosphatiylcholine (DOPC), dipalmitoyl-phosphatidylcholine (DPPC), dipalmitoyl phosphatidyl glycerol (DPPG), dipalmitoyl phosphatidic acid (DPPA), distearoyl phosphatidyl ethanolamine (DSPE), dimyristoyl-phosphatidyl choline (DMPC), diacyl phosphatidyl glycerols, such as dimyristoyl phosphatidyl glycerol (DMPG), dipalmitoyl phosphatidyl glycerol (DPPG), and distearoyl phosphatidyl glycerol (DSPG), diacyl phosphatidyl cholines, such as dimyristoyl phosphatidylcholine (DMPC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DMPE), dipalmitoyl phosphatidyl ethanolamine (DPPE) and distearoyl phosphatidyl ethanolamine (DSPE), distearoylphosphatidylethanolamine-polyethyleneglycol (DSPE-PEG), dipalmitoylphosphatidylethanolamine-polyethyleneglycol (DPPE-PEG), dioleoylphosphatidylethanolamine-polyethyleneglycol (DOPE-PEG), wherein the PEG chain can range from 200 Da to 10000 Da molecular weight, but more likely greater than 350 Da and less than 5000 Da. Preferably, PEG chain lengths would be in the range of 1 kDa to 5 kDa molecular weight. Additionally, while one end of the PEG chain is joined to the lipid species, the other end of the PEG chain may be functionalized by other groups such as a methyl group, carboxylic acid group, N-hydroxysuccinimide group, maleimide groups, cyanur group, etc, to impart chemical functionality to the outer surface of the encapsulated particle, or to facilitate further chemical modification of the PEG chain, for instance to attach a targeting species.

Sphingolipids are lipid molecules with a backbone consisting of a sphingoid base (itself containing an acyl chain) to which is bound a fatty acyl chain and a headgroup. The fatty acyl chain can contain 6-24 carbons, and may be branched or unbranched. This chain can contain 1 or more double bonds and/or one or more triple bonds and be cis or trans isomers. Chains of 12 to 24 carbons are preferred. Headgroups can, for example, be hydrogen yielding ceramides, or phosphocholine yielding sphingomyelin. A preferred embodiment of the invention includes sphingomyelin.

Stabilization coatings of the invention can consist of inorganic oxides. Such inorganic oxides may include semiconductor oxides and oxides of transition metals. Two examples of such oxides are silicon or titanium. These oxides would be nucleated and deposited on the surface of the dye-coated nanoparticles in a shell with a thickness of 1-100 nm but more likely in the range of 5-20 nm. While not being bound by any theory or speculation, it is believed that confining the dye aggregate close to the metal nanoparticle keeps the dye molecules communicating with each other in the aggregate and the metal nanoparticle. By confining and maintaining the aggregate in contact with the metal nanoparticle advantageously results in suppression of fluorescence.

Ligands Bound to Stabilization Coating Layer

A SERS complex of the invention can include an additional ligand, one that has the ability to recognize and bind to partner of the ligand. A SERS complex having such a ligand can thus bind to the ligand partner. An example of such a ligand, one illustrated by results described herein, is an antibody (SERS complex ligand) which binds to an antigen (target).

In the results illustrated by laboratory examples carried out and described herein, the ligand was incorporated into an already prepared SERS complex. In one example, the SERS complex was prepared with a phosholipid containing a functional group to which the ligand could be covalently linked. The ligand was then linked to the functional group of the phospholipid in the encapsulating layer of the SERS complex. In another example, the ligand was linked to a phosholipid that was subsequently incorporated into the encapsulating layer of an existing SERS complex. Yet another example uses a ligand that is attached to a silica shell which encapsulates the existing SERS complex. Each approach successfully produced SERS complexes having ligands that were able to recognize their targets. The skilled person will recognize here that an anchor covalently linked to the ligand is not necessarily a phospholipid but that it has to be e.g., a molecule compatible with the encapsulating layer of the SERS complex so that it can stably incorporated into or conjugated onto said layer.

Various types of moieties that can act as a ligand when covalently linked to a component of the encapsulating layer of the SERS complex are a nucleotide, a nucleic acid molecule, a DNA molecule, an RNA molecule, an aptamer, a peptide, a protein, an amino acid, a lipid, a carbohydrate, a drug, a drug precursor, a drug candidate molecule, a drug metabolite, a vitamin, a synthetic polymer, a receptor ligand, a metabolite, an immunoglobulin, a fragment of an immunoglobulin, a domain antibody, a monoclonal antibody, a VH domain, a VL domain, a single chain antibody, a nanobody, a unibody, a monobody, an affibody, a DARPin, an anticalin, a $^{10}$Fn3 domain, a versabody, a Fab fragment, a Fab' fragment, an Fd fragment, an Fv fragment, an F(ab')$_2$ fragment, and an Fc fragment, a proteinaceous binding molecule having an antibody-like function, a glubody, a protein based on the ankyrin scaffold or the crystalline scaffold, an AdNectin, a tetranectin, an avimer, a peptoid, or a cell surface marker.

A ligand can alternatively be defined in terms of the moiety or target with which it binds or which it selectively captures. A ligand can thus be one that selectively binds to a cell, a virus, bacteria, a spore, a toxin, a protein, a peptide, and amino acid, an antigen, a lipid, a nucleic acid, a polynucleotide, an oligonucleotide, a drug, or an explosive.

The skilled person will appreciate that e.g., an antibody can be linked to the SERS complex so as to target an antigen, in one context, while in another context, an antigen might be linked to the SERS complex as a ligand which targets an antibody.

Phospholipids of the encapsulating layer of a SERS complex of the invention are amphipathic. Hydrophilic portions of phosholipids are situated towards the exterior of the layer and a ligand is linked so that it can effectively recognize its partner. In one of the examples described herein, COOH-PEG-DSPE (DSPE=distearoyl phosphatidylethanolamine) was incorporated into the encapsulating phospholipid layer during production of the SERS complex. The carboxyl group was then activated and covalently coupled to an antibody in a conventional manner. In another example, a F(ab')$_2$ fragment was generated and covalently linked to maleimide-PEG-DSPE through the thiol group of the cysteine residue of the fragment. The F(ab)-PEG-DSPE was then incubated with a SERS complex to be incorporated into its encapsulating layer. The skilled person thus appreciates that the ligand is linked in these cases to the outwardly located lipid headgroup and oriented outwardly of the to phospholipid layer of the SERS complex to permit binding with the target of the ligand.

Encapsulation of Nanoparticle Composites by Lipid Bilayers

Given the foregoing results, the skilled person would be capable of practising the invention in its various aspects, including variations as described below.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An excitonic semiconductor noble metal composite nanoparticle for enhanced Raman scattering, comprising:
   a noble metal nanoparticle having a surface;
   a layer of linker molecules being bound to the surface of the noble metal nanoparticle, wherein said linker molecules include a thiol, such that the linker molecules are attached to the surface of the noble metal nanoparticle via the thiol;
   a layer of dye molecules having an absorption band and being bound to the layer of linker molecules with mobility on the layer of the linker molecules, said dye molecules being selected such that the individual dye molecules align and aggregate into a J-aggregate ordered dye structure, where the exciton of the J-aggregate ordered dye structure results in an absorption band that is narrower than that of the monomeric species of said dye, exhibiting a further collective coupling to the noble metal nanoparticle surface plasmon when said J-aggregate ordered dye structure is bound to the noble metal nanoparticle through the linker molecules; and
   a stabilizing and fluorescence-reducing coating encapsulating the noble metal nanoparticle having the linker layer and the ordered structure of dye molecules bound thereto, to produce an encapsulated composite nanoparticle;
   wherein said encapsulated composite nanoparticle exhibits enhanced Raman scattering compared to nanoparticles having the dye molecules bound thereto not in said ordered structure, and
   wherein said J-aggregate ordered dye structure has a dielectric constant having wavelength dependent real and imaginary parts value which are
   approximately equal and
   approach zero at a given wavelength,
   and wherein excitation of said composite by a laser excitation source having a wavelength near the given wavelength results in an enhance SERS signal compared to excitation of the same nanoparticle in which the dye does not form an ordered structure, where the exciton of the J-aggregate ordered dye structure results in an absorption band that is narrower than that of the monomeric species of that dye, exhibiting a further collective coupling to the noble metal particle surface plasmon when said J-aggregate ordered dye structure is bound to the noble metal nanoparticle through the linker molecules.

2. The semiconductor noble metal composite nanoparticle according to claim 1 wherein said noble metal nanoparticles are any of gold, silver, copper, nickel, palladium, platinum, ruthenium, rhodium, osmium, iridium, or an alloy of any of the foregoing metals.

3. The semiconductor noble metal composite nanoparticle according to claim 1 wherein said linker molecules have a length in a range from about 0.1 nm to about 10 nm.

4. The semiconductor noble metal composite nanoparticle according to claim 1 wherein said dye includes any one of polymethine dye, where the polymethine dye may be, but not limited to, a cyanine dye, including but not limited to merocyanines, indocyanines, anthrocyanines, phycocyanine, isocyanines, pseudoisocyanines and thiacyanines; squaraines; perylene bisimides; any of the above in combination, e.g. a squaraine and a cyanine conjugated together.

5. The semiconductor noble metal composite nanoparticle according to claim 1 wherein said dye includes all classes of cyanine dye that form J-aggregates, H-aggregates, aggregates in which a collective absorption of the aggregate is different than that of the monomeric species of that dye.

6. The semiconductor noble metal composite nanoparticle according to claim 1, including a ligand covalently linked to the stabilizing coating encapsulating a nanoparticle.

7. The semiconductor noble metal composite nanoparticle according to claim 6, wherein the ligand is an antibody or an antibody fragment.

8. The semiconductor noble metal composite nanoparticle according to claim 6, wherein the ligand is any one or combination of monoclonal antibodies and other targeting ligands to selectively target cell surface receptors and sub-cellular markers.

9. The semiconductor noble metal composite nanoparticle according to claim 8, wherein said other targeting ligands includes any one or combination of antibody fragments, peptides, DNA, RNA, proteins, affabodies, monobodies, drugs, cell surface markers, and sub-cellular markers.

10. The semiconductor noble metal composite nanoparticle according to claim 1 wherein said encapsulated dye aggregate coated noble metal nanoparticles are conjugated to monoclonal antibodies and other targeting ligands using one or both of physical and chemical means of associating these with either the gold particle core, or the phospholipid encapsulating said gold nanoparticles.

11. The semiconductor noble metal composite nanoparticle according to claim 1, wherein the nanoparticle is for a biosensor or chemical sensor.

12. The semiconductor noble metal composite nanoparticle, according to claim 1, wherein the nanoparticle is for vibrational spectroscopy, or for near field IR spectroscopy.

13. The semiconductor noble metal composite nanoparticle according to claim 1 wherein said stabilizing coating is an inorganic oxide.

14. The semiconductor noble metal composite nanoparticle according to claim 13, wherein said stabilizing coating further includes a lipid bilayer, said lipid bilayer being any one of phospholipid alone, sphingolipid alone, phospholipid and sphingolipid, phospholipid and sterol, sphingolipid and sterol, phospholipid and sphingolipid and sterol, wherein said phospholipid is one type or a mixture of phospholipids, said sphingolipid is one type or a mixture of sphingolipids, and said sterol is one type or a mixture of sterols, to form a mixture.

15. The semiconductor noble metal composite nanoparticle according to claim 14 wherein said phospholipids have one or more hydrocarbon chain(s) being any one or combination of saturated, monounsaturated, and polyunsaturated.

16. The semiconductor noble metal composite nanoparticle according to claim 14 wherein said sphingolipids have one or more hydrocarbon chain(s) being any one or combination of saturated, monounsaturated, and polyunsaturated.

17. The semiconductor noble metal composite nanoparticle according to claim 14 wherein said phospholipids and sphingolipids have headgroups which are any one of phosphatidyl choline (PC), phosphatidyl ethanolamine (PA), phosphatidyl inositol (PI), and phosphatidyl glycerol (PG).

18. The semiconductor noble metal composite nanoparticle according to claim 14 wherein said phospholipids, sphingolipids and sterols have headgroups can be positively charged, negatively charged, zwitterionic, or neutral.

19. The semiconductor noble metal composite nanoparticle according to claim 14 wherein said phospholipids, sphingolipids and sterols include chemically modified tail groups and/or chemically modified headgroups.

20. The semiconductor noble metal composite nanoparticle according to claim 14 wherein said phospholipids are any one or combination of naturally occurring or synthetic, and wherein said sphingolipids are any one or combination of naturally occurring or synthetic, and wherein said sterols are any one or combination of naturally occurring or synthetic.

21. The semiconductor noble metal composite nanoparticle according to claim 14 including detergent molecules present in a suspension of lipids into which the nanoparticles are immersed to form the lipid bilayer around said nanoparticles.

22. The semiconductor noble metal composite nanoparticle according to claim 14 including controlling a distribution of charged lipids in said lipid bilayer by addition of acids and/or salts in a suspension of lipids into which the nanoparticles are immersed to form the lipid bilayer around said nanoparticles.

23. The semiconductor noble metal composite nanoparticle according to claim 14 wherein lipid encapsulated dye aggregate coated noble metal nanoparticles are separated from unbound phospholipids and organic dye molecules by centrifugation.

24. The semiconductor noble metal composite nanoparticle according to claim 14 wherein said dye aggregate coated noble metal nanoparticles are capped by positively or negatively charged ligands with any and all combinations of lipids.

25. The semiconductor noble metal composite nanoparticle according to claim 14, where the ordered structure-forming dye is housed within the bilayer structure itself, on either surface of the bilayer, or the use of an ordered structure-forming dye modified so as to be conjugated physically to a lipid component.

26. The semiconductor noble metal composite nanoparticle according to claim 14 wherein the stabilization coating has a thickness in a range from about 0.1 nm to about 100 nm.

27. The semiconductor noble metal composite nanoparticle according to claim 14 wherein the stabilization coating has a thickness in a range from about 0.1 nm to about 10 nm.

28. The semiconductor noble metal composite nanoparticle according to claim 13 wherein said inorganic oxide is a semiconductor oxide.

29. The semiconductor noble metal composite nanoparticle according to claim 13 wherein said inorganic oxide is an oxide of a transition metal.

30. The semiconductor noble metal composite nanoparticle according to claim 13 wherein the stabilization coating has a thickness in a range from about 0.1nm to about 100 nm.

31. The semiconductor noble metal composite nanoparticle according to claim 13 wherein the stabilization coating has a thickness in a range from about 5 nm to about 20 nm.

32. The semiconductor noble metal composite nanoparticle according to claim 1, wherein said stabilizing coating is an oxide of any one of silicon, titanium and mixtures thereof.

33. The semiconductor noble metal composite nanoparticle according to claim 1 wherein said linker molecules include any one or a combination of thiocholine, trimethyl-ammonium conjugated alkanethiols, 2-mercaptopropionic acid, 16-mercaptohexadecanoic acid, and glutathione.

* * * * *